(12) United States Patent
Hascoet et al.

(10) Patent No.: US 6,506,159 B2
(45) Date of Patent: Jan. 14, 2003

(54) METHOD AND APPARATUS FOR IMPROVING THE ACCURACY WITH WHICH THE SPEED OF A FLUID IS MEASURED

(75) Inventors: Gerard Hascoet, Paris (FR); Thierry Pechoux, Paris (FR)

(73) Assignee: Arrow International, Inc., Reading, PA (US)

(*) Notice: Subject to any disclaimer, the term of this patent is extended or adjusted under 35 U.S.C. 154(b) by 0 days.

(21) Appl. No.: 09/922,603

(22) Filed: Aug. 3, 2001

(65) Prior Publication Data

US 2002/0042575 A1 Apr. 11, 2002

Related U.S. Application Data

(63) Continuation of application No. 09/522,089, filed on Mar. 10, 2000, now Pat. No. 6,287,260.

(51) Int. Cl.[7] .............................................. A61B 8/00
(52) U.S. Cl. ....................................................... 600/454
(58) Field of Search ................................. 600/454, 455, 600/456, 443, 447, 448, 460, 461, 465, 457

(56) References Cited

U.S. PATENT DOCUMENTS

| | | | |
|---|---|---|---|
| 5,409,010 A | * | 4/1995 | Beach et al. ............... 600/455 |
| 5,488,953 A | * | 2/1996 | Vilkomerson ............... 310/334 |
| 6,261,233 B1 | * | 7/2001 | Kantorovich ............... 600/454 |

* cited by examiner

Primary Examiner—Marvin M. Lateef
Assistant Examiner—Maulin Patel
(74) Attorney, Agent, or Firm—Amster, Rothstein & Ebenstein

(57) ABSTRACT

The present invention relates to a method and associated apparatus for improving the accuracy with which the speed of a fluid, such as a liquid, in particular blood flowing in a duct, such as a blood vessel, in particular the aorta, is measured by means of a signal emitted by a Doppler transducer (4). In characteristic manner, according to the method, the Doppler transducer is associated with a programmable memory (50) which contains at least one correction data item for correcting the Doppler signal transmitted by the transducer (4) to a transducer control and computer unit (8). Said computer unit (8) incorporates said signal correction data item in its computation (at 16) of each speed measurement on the basis of each signal emitted by the Doppler transducer, and it computes the speed value while taking account of said correction data item so as to provide a corrected measurement of the speed of said fluid, thereby improving its accuracy.

14 Claims, 3 Drawing Sheets

FIG_1

METHOD AND APPARATUS FOR IMPROVING THE ACCURACY WITH WHICH THE SPEED OF A FLUID IS MEASURED

This is a continuation of application Ser. No. 09/522,089, filed Mar. 10, 2000, now U.S. Pat. No. 6,287,260.

The present invention relates essentially to a method and to apparatus for improving the accuracy with which the speed of a fluid, such as a liquid, in particular blood flowing in a duct, such as a blood vessel, in particular the aorta, is measured by means of a signal emitted by a Doppler transducer.

BACKGROUND OF THE INVENTION

Document FR-A-2 424 733 INSERM discloses an ultrasound intracorporeal probe that is inserted into the esophagus to measure the flow rate in the aorta. That prior probe is characterized by a catheter structure whose distal portion has a bag that can be inflated from the outside with a liquid and that surrounds the ultrasound emitter which is housed entirely inside the bag which serves to prevent the emitter from moving inside the duct and which serves to couple the emitter acoustically. The emitter is mounted to rotate inside said inflatable bag on a support block which is disposed substantially on the longitudinal axis of the probe, and it is rotated by a flexible cable connected at its proximal end at the outside to rotary drive means, e.g. in the form of a knob (see the claims and the corresponding text describing the figures, in particular page 2, line 24 to page 4, line 29).

That prior INSERM document has been improved in the context of document U.S. Pat. No. 5,479,928 according to which the intracorporeal probe has in combination: at least one broad-beam ultrasound transducer fixed on the support block in such a manner as to be oriented at an angle of inclination that is not perpendicular relative to the longitudinal axis of the probe; and at least one narrow beam ultrasound transducer fixed on the support block so as to be oriented at an angle that is essentially perpendicular relative to the longitudinal axis of the probe so as to be oriented substantially perpendicularly relative to the longitudinal axis of a duct in which the speed of a liquid is to be measured, and in particular the flow rate of the liquid, specifically the flow rate of blood when the duct is a blood vessel.

The improvement according to that document is entirely satisfactory and is available on the market from SOMETEC under the trade name DYNEMO 3000®.

OBJECTS AND SUMMARY OF THE INVENTION

A main object of the present invention is to resolve the novel technical problem consisting in supplying a solution enabling account to be taken of each feature of the Doppler transducer in order to improve the accuracy with which the speed of a fluid, such as a liquid, is measured by means of a signal emitted by such a Doppler transducer.

Another main object of the present invention is to supply a solution making it possible also to take account of the 3D position of a Doppler transducer, and in particular the angle at which it emits the ultrasound beam, thereby improving the accuracy with which the speed of a fluid, such as a liquid, is measured by means of the signal emitted by such a Doppler transducer.

Another main object of the present invention is to resolve the said novel technical problems in a manner that is particularly simple, low cost, reliable, and usable on a medical and industrial scale.

Those problems are resolved for the first time by the present invention at low manufacturing cost by means of a design that is particularly simple, using a small number of parts, while conserving the operating advantages of prior art probes, in particular the improved probe constituting the subject matter of document U.S. Pat. No. 5,479,928, and sold in the form of the DYNEMO 3000® appliance.

In a first aspect, the present invention provides a method of improving the accuracy with which the speed of a fluid, such as a liquid, in particular blood flowing in a duct, such as a blood vessel, in particular the aorta, is measured by means of a signal emitted by a Doppler transducer, the method being characterized in that the Doppler transducer is associated with a programmable memory which contains at least one correction data item for correcting the Doppler signal transmitted by the transducer to a transducer control and computer unit, in that said computer unit incorporates said signal correction data item in its computation during each speed measurement on the basis of each signal emitted by the Doppler transducer, and computes the speed value while taking account of said correction data item, so as to provide a corrected measurement of the speed of said fluid, thereby improving the accuracy of the measurement.

According to an advantageous characteristic of the method, it is characterized in that said Doppler transducer is incorporated or integrated in a probe, in particular an intracorporeal Doppler effect probe, said Doppler transducer being mounted on the probe to emit an ultrasound beam at an angle relative to the longitudinal axis of the probe; and in that said probe also comprises said programmable memory.

According to another advantageous implementation of the method, it is characterized in that said programmable memory also contains at least one sensitivity data item for informing the user of loss of sensitivity to the Doppler signal, and in that said transducer control and computer unit verifies said sensitivity data item present in the programmable memory on each measurement of the signal transmitted by the transducer in order to verify that the sensitivity as actually obtained on a signal transmitted by the transducer is not too far removed from the sensitivity value present in the programmable memory, and on going beyond a specified limit value, said transducer control and computer unit issues a signal to the user indicative of a loss of sensitivity.

According to yet another advantageous characteristic of the invention, the method is characterized in that the said signal correction data item is obtained on the basis of tests, preferably performed at the manufacturing site, while performing preliminary use tests on the Doppler transducer in order to verify the reliability of its signal.

According to another advantageous characteristic of the method of the invention, it is characterized in that the sensitivity data item is obtained during tests, preferably performed at the manufacturing site, while measuring the flow speed of a fluid that is flowing at a known speed.

According to yet another advantageous characteristic of the method of the invention, the method is characterized in that the signal correction data item comprises at least the angle at which the Doppler beam is emitted by the Doppler transducer relative to the axis of the probe, so that the speed value takes account of said real working angle of the beam from the Doppler transducer.

Advantageously, the sensitivity data comprises at least one average of a plurality of sensitivity measurements obtained with a corresponding number of uses of the Doppler transducer, each sensitivity measurement resulting from the amplitude of the signal received from the transducer.

According to another advantageous characteristic of the method of the invention, it is characterized in that the transducer control and computer unit continuously computes the mean of a plurality of recently calculated sensitivity measurements and compares it with the sensitivity mean initially written as sensitivity data in the programmable memory, and, beyond a certain difference relative to the initially programmed sensitivity measurement, issues a signal to the user indicative of a loss of sensitivity.

According to yet another advantageous characteristic of the invention, the method is characterized in that when the Doppler transducer operates in combination with an additional transducer, e.g. for measuring the diameter of a duct in which said fluid flows, at least one sensitivity data item relating to said additional transducer is preferably also provided in said programmable memory in order to verify its sensitivity over time and likewise issue a signal to the user in the event of sensitivity being lost.

In a second aspect, the present invention also provides an apparatus for improving the accuracy with which the speed of a fluid, such as a liquid, in particular blood flowing in a duct, such as a blood vessel, in particular the aorta, is measured by means of a signal emitted by a Doppler transducer, the apparatus being characterized in that it comprises a programmable memory containing at least one correction data item for correcting the Doppler signal transmitted by the transducer to a transducer control and computer unit, and in that means are provided to enable the computer unit to incorporate said signal correction data item in computing each speed measurement on the basis of each signal emitted by the Doppler transducer and to compute the speed value taking account of said correction data item so as to provide a corrected measurement of the speed of said fluid, thereby increasing its accuracy.

In an advantageous embodiment, said Doppler transducer is incorporated or integrated in a probe, in particular in a Doppler effect intracorporeal probe, said Doppler transducer being mounted on the probe to emit its ultrasound beam at an angle relative to the longitudinal axis of the probe; and said probe also comprises said programmable memory connected to said control and computer unit, which memory is thus secured to the probe and is dedicated thereto.

In another advantageous embodiment of the invention, said programmable memory also contains at least one sensitivity data item for informing the user of a loss of sensitivity in the Doppler signal, and the transducer control and computer unit verifies said sensitivity data item present in the programmable memory on each measurement of the signal transmitted by the transducer in order to verify that the sensitivity actually obtained on the signal transmitted by the transducer is not too far removed from the sensitivity value present in the programmable memory; signal-issuing means are provided; and in the event of sensitivity going beyond a set limit value, the transducer control and computer unit issues a signal to the user via said signal-issuing means to inform the user of a loss of sensitivity.

In another advantageous embodiment of the invention, said signal correction data item is obtained from tests preferably performed at the manufacturing site while performing preliminary use tests on the Doppler transducer in order to verify the reliability of its signal.

According to another advantageous characteristic of the invention, the sensitivity data item is obtained during tests that are preferably performed at the manufacturing site while measuring the flow speed of a fluid that is flowing at a known speed.

According to another advantageous characteristic, the signal correction data item comprises at least the angle at which the Doppler beam is emitted by the Doppler transducer relative to the axis of the probe, so that the speed value takes account of said real working angle of the beam from the Doppler transducer as actually mounted on the probe.

According to another advantageous characteristic of the invention, the sensitivity data item comprises at least an average of a plurality of sensitivity measurements obtained over a corresponding number of uses of the Doppler transducer, each sensitivity measurement resulting from the amplitude of the signal received from the transducer.

According to another advantageous characteristic of the invention, the transducer control and computer unit continuously computes the mean of a plurality of recently calculated sensitivity measurements and compares it with the sensitivity mean initially entered as sensitivity data into the programmable memory and beyond a certain difference relative to the initially programmed sensitivity measurement, issues a signal to the user via said signal-issuing means to indicate a loss of sensitivity.

According to another advantageous characteristic of the invention, said apparatus further comprises an additional transducer operating in combination with the Doppler transducer, said additional transducer being intended, for example, to measure the diameter of a duct in which said fluid flows, said programmable memory preferably further containing at least one sensitivity data item concerning said additional transducer so as to verify its sensitivity over time and likewise issue, via said signal-issuing means, a signal to the user in the event of a loss of sensitivity.

It will thus be understood that by means of the invention all of the previously-mentioned advantages are obtained.

BRIEF DESCRIPTION OF THE DRAWINGS

Other objects, characteristics, and advantages of the invention appear clearly from a presently preferred embodiment of the invention given merely by way of example and which does not limit the scope of the invention in any way. In the drawings.

PREFERRED EMBODIMENT OF THE INVENTION

Figure 1:
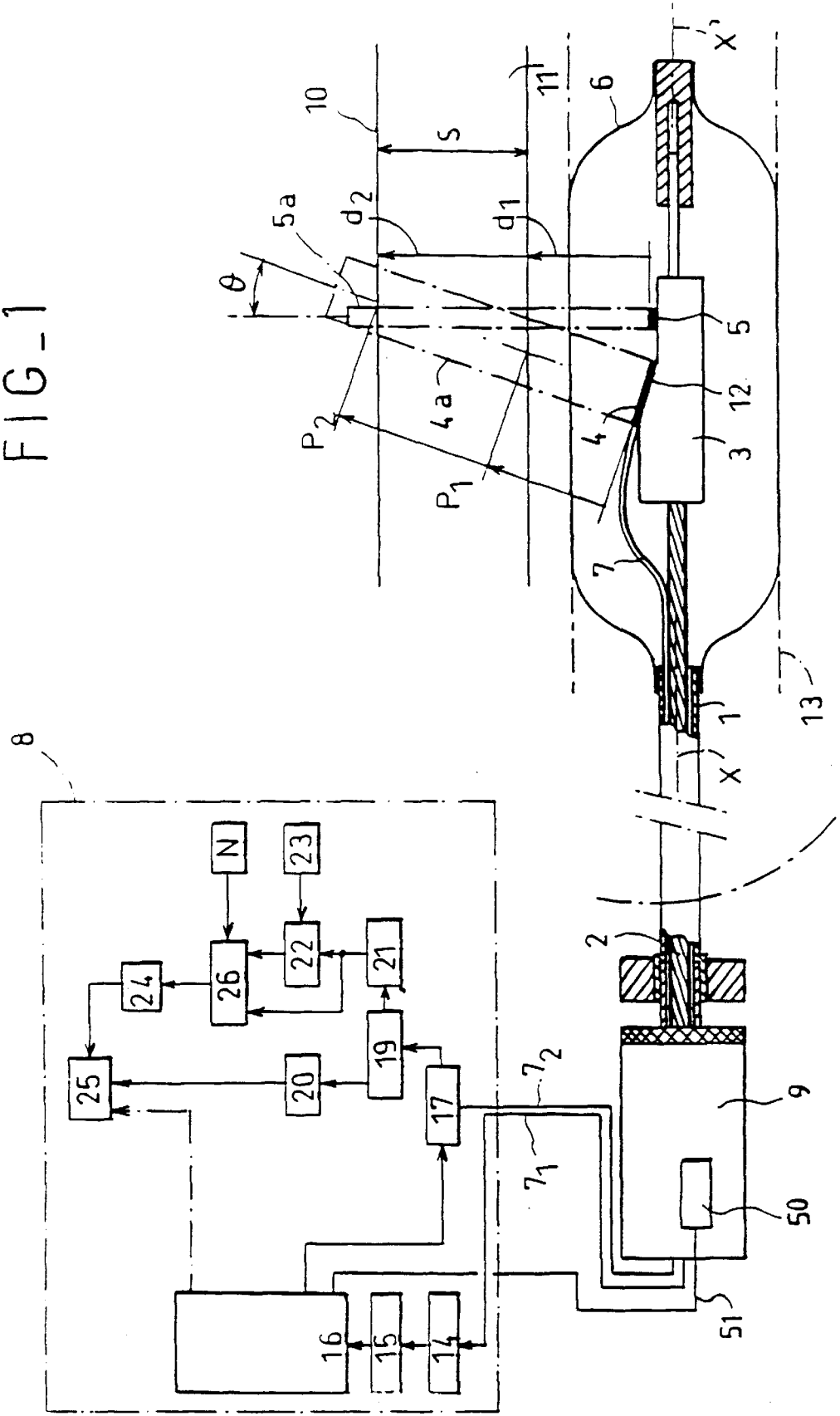
FIG. 1 shows a probe comprising a Doppler transducer in accordance with FIG. 1 of patent U.S. Pat. No. 5,479,928, but modified to incorporate a programmable memory in accordance with the present invention, the probe being shown in cross-section and in elevation, and, as in FIG. 1 of patent U.S. Pat. No. 5,479,928, in its working position in the esophagus facing a blood vessel, in this case the aorta 10.

FIG. 1 reproduces FIG. 1 of U.S. Pat. No. 5,479,928= FR-A -2,695,999=EP-A-0,595,666 and uses essentially the same reference numerals. With reference to FIG. 1, a catheter-shaped probe 1 for measuring the speed of flow of a fluid F is manufactured in conventional manner. For example, the probe is preferably intended to measure the speed of flow of blood in the aorta 10, with the probe 1 comprising a Doppler transducer 4 having a broad beam 4*a* and being, by way of example, of the same type as that described in patent U.S. Pat. No. 5,479,928=FR-A-2,695,999=EP-A-0,595,666, to which the person skilled in the art can refer.

In this preferred embodiment, the Doppler transducer 4 is designed on manufacture to present an angle of inclination for its ultrasound beam of 60° relative to the longitudinal axis x–x' of the probe 1.

Incidentally, and preferably, the Doppler transducer 4 operates in combination with an additional transducer 5, for example and preferably in the context of measuring the flow speed of blood in a blood vessel, in this case the aorta 10, a transducer which produces a narrow beam 5*a* as described in document U.S. Pat. No. 5,479,928, with the transducer being placed parallel to the longitudinal axis of the probe so that its ultrasound beam extends perpendicularly to the longitudinal axis of the probe for the purpose of measuring the diameter and thus the flow section S of the duct 10 in which there flows the fluid F whose speed is to be measured, as described in the above-specified documents and as is also known to the person skilled in the art, in particular from those documents.

The other references in FIG. 1 which are identical to those of FIG. 1 in U.S. Pat. No. 5,479,928=FR-A-2,695,999=EP-A-0,595,666 have the following meanings: reference numeral 1 represents the outside portion of the catheter-shaped probe which, when installed in a duct, in this case the esophagus 13 facing a blood vessel, in this case the aorta 10, will take up a position that is fixed once the inflatable balloon 6 has been inflated in the manner known to the person skilled in the art.

The catheter-forming probe 1 has an internal flexible cable 2 connected at one of its ends to the support block 3 on which the ultrasound transducers 4 and 5 are mounted. The transducers 4 and 5 are connected to an electric cable 7 placed in the probe 1 at its distal end and leaving the probe 1 on the outside for connection to a computer center or unit for controlling the transducers and for processing the signals they deliver. The external end of the flexible cable 2, remote from its end connected to the support block 3, is connected to a drive member 9, in this case modified in accordance with the present invention to be in the form of a handle suitable for being taken hold of to rotate the flexible cable 2 appropriately about its own axis so as to rotate the support block 3, thereby directly turning the ultrasound beams 4*a* and 5*a* respectively of the transducers 4 and 5 appropriately relative to the duct 10 such as the aorta in which it is desired to measure the flow speed of the fluid F, in this case blood. The control and computer unit 8 comprises, as described in U.S. Pat. No. 5,479,928 and its equivalents, means 14 connected to the transducer 5 by a link $7_1$ designed to determine the amplitudes of echo signals received by the narrow beam transducer 5. These determination means 14 are connected to means 15 designed to detect the amplitude maxima in the reflected signals.

Means 16 are also provided in the control and computer unit 8 to determine the range $P_2$–$P_1$ circumscribing the section of the duct 10 at two opposite extreme points by taking account solely of the echoes of the transducer 5 coming from said range $P_2$–$P_1$. The means 16 are connected to the means 15 in order to determine the range $d_2$–$d_1$ which corresponds to the two extreme points of the duct, in this case the aorta 10, as detected by the amplitude maxima in the reflected echoes of the signals from the transducer 5. By knowing the range $d_2$–$d_1$, it is possible to calculate the flow section S since it is conventional to consider the duct 10, in this case the aorta, to be circular in section. The means 16 which conventionally comprise a microcomputer with appropriate software also takes account of the angle of inclination θ between the two beams 4*a* and 5*a* as shown in FIG. 1 and as known, in particular by construction. These means 16 control selection means 17 connected to the transducer 4 by a link $7_2$. The means 17 make it possible to select only those echoes of signals from the transducer 4 which are obtained over a response time interval corresponding to the range $P_2$–$P_1$. The selection means 17 are connected to conventional signal processing means 19 for obtaining a Doppler signal. These processing means 19 are also connected to conventional means 20 suitable for determining the mean speed $V_m$ of the fluid F, in this case blood, as averaged over the section S of the duct 10, in this case the aorta.

As described in U.S. Pat. No. 5,479,928, the unit 8 also has means 21 suitable for measuring the energy backscattered by moving particles, in this case red corpuscles in the blood. The output from the measuring means 21 is connected to means 22 designed to allow backscattered energy to pass through at one or more defined instants, in particular during systole when measuring blood speed, said means 22 also being connected to means 23 suitable for determining those defined instants, and in particular the instant at which systole occurs when blood is being measured. The means 22 deliver the value of the backscattered energy $E_S$ during systole when measuring blood.

As described in U.S. Pat. No. 5,479,928, outside systole and in particular during diastole, the area $S_D$ covered by the particles actually in motion is likely to be smaller than the full section S.

By taking account of backscattered energy during systole $E_S$ and during diastole $E_D$ it is possible to determine the real flow section or the effective ideal section $S_D$ involved in the flow rate. This area is defined by the following mathematical equation:

$$S_D = S \cdot (E_D/E_S) = S \cdot K$$

The correction factor K is determined by correction means 24 connected to the means 21 and 22. The correction means 24 weight the factor K by an empirical correction factor which takes account of the technical characteristics of the transducer 4 in use and of the means 19, in particular the minimum value of the speeds detected and the passband of the emitted Doppler signal. The correction means 24 are connected to means 25 that are also connected to the means 20 for determining the mean speed over the section. The means 25 make it possible to calculate a corrected mean speed $V_c$ using the values for the mean speed over the area and the correction factor K, and thus to calculate the flow rate of the fluid F, in this case blood, moving through the localized area $S_D$, given knowledge of the section S of the duct 10, in this case the aorta, as measured from distances $D_1$ and $D_2$ obtained by the transducer 5 disposed perpendicular to the duct 10.

In an embodiment, the correction factor K can be represented by the following equation:

$$K = \left(\frac{E_D}{E_S}\right)^n \times k$$

in which:
  K=correction factor;
  $E_D$=partial backscattered energy as defined above;

$E_S$=total backscattered energy as defined above;

n is a number constituting another corrector factor; and k is a correction factor as defined above depending on the technical characteristics of the Doppler transducer 4 and of the means that emit, receive, measure, and process the signals associated with the Doppler effect transducer 4, including the measurement means 19.

In the context of the present invention, in order to improve the accuracy with which the speed of the fluid is measured, provision is made for the apparatus that comprises the probe 1 and its control and computer unit 8 to further comprise, in accordance with the present invention, a programmable memory 50 which is associated with the Doppler transducer 4 and which contains at least one data item for correcting the Doppler signal transmitted from the transducer 4 to the transducer control and computer unit 8, and in particular to its computation means 16. Such programmable memories are commercially available, e.g. memories known as EEPROMs or memories known as flash memories. The computation means 16 conventionally comprise, for example, a computer or a microcomputer having appropriate software for controlling it. In this context, the computation means 16 also has software incorporating said signal correction data item as recorded in the programmable memory 50 each time it performs computations on each speed measurement as obtained by means of the Doppler transducer 4.

According to a preferred characteristic of the invention, this signal correction data item comprises at least the angle θ at which the ultrasound beam is emitted by the Doppler transducer 4. This angle is determined by performing a plurality of speed measurements using the Doppler transducer 4 on a fluid that is flowing along a calibrated duct of known diameter at a known speed of fluid flow which is preferably adjusted to a different known speed value for each measurement.

As is well known to the person skilled in the art, the flow speed of the fluid as obtained by the Doppler effect is derived from the mathematical equation:

$$V \approx \frac{\Delta F}{F_{emit}} \times \frac{C}{2 \cdot \cos(\theta)}$$

in which:

ΔF=the frequency difference between reception and emission, as a result of the Doppler effect;

$F_{emit}$=the frequency at which the ultrasound beam is emitted by the Doppler transducer;

C=the speed of propagation of sound in the medium, e.g. in blood, equal to 1584 meters per second (m/s); and θ=the angle at which the ultrasound beam is emitted by the Doppler transducer 4 relative to the longitudinal axis x–x' of the probe 1.

As a result, starting from the speed value as actually measured and starting from an average of a plurality of speed measurements at different flow speeds, the exact value of the angle at which the ultrasound beam is emitted by the Doppler transducer is obtained, i.e. as emitted by the probe.

This angle θ is thus incorporated in the programmable memory 50 for subsequent use by the computer unit 8 in calculating the real speed when measuring the speed of a fluid F flowing along a given duct 10, in particular and preferably the aorta. Preferably, the programmable memory is incorporated in or forms an integral portion of the probe 1, thus having the advantage of constituting a "signature" for the probe.

According to another advantageous characteristics of the invention, the programmable memory 50 also includes data concerning the sensitivity of the Doppler transducer 4.

This sensitivity data is obtained by programming the transducer control and computer unit 8 which, on each speed measurement, memorizes the amplitude of the signal received by the transducer after a Doppler emission, and takes an average over a plurality of measurements to calculate a reference sensitivity which is subsequently stored by the computer unit 8 in the programmable memory 50 and which is subsequently used as an initial reference sensitivity, the control and computer unit 8 subsequently and on each measurement recalculating the sensitivity of the Doppler transducer 4 and preferably also taking an average over a plurality of measurements, which it compares with the initial sensitivity, such that in the event of too great a difference, e.g. greater than ±10% relative to the initial sensitivity measurement, the control and computer unit 8 issues a signal to the user to inform the user that there has been a loss of sensitivity. By way of example, this signal can be an alarm, or a warning lamp, or a message.

For example, it is possible to use the rms value of the received electrical signal. By way of example, this value is about 50 μV for a conventional Doppler transducer 4 having dimensions of 3 mm×4 mm and operating at about 5 MHz.

When an additional transducer 5 is used, in particular and preferably for measuring the diameter of the duct 10 in which the fluid F is flowing, the sensitivity of the additional transducer 5 is measured in the same manner, and this sensitivity measurement is also put into the programmable memory 50 so as to be able to give the user a similar signal concerning loss of sensitivity for this additional transducer, when appropriate. By way of example, the initial sensitivity value may be 80 μV for an additional transducer 5 having a diameter of 3 mm and operating at a frequency of about 10 MHz.

It will thus be understood that the invention makes it possible to monitor proper operation of the Doppler transducer 4 and possibly also of the additional transducer 5 effectively and to inform the user, or to monitor any other additional transducer that may be present on the probe.

In the context of the invention, any commercially available programmable memory can be used. Examples of programmable memories that are presently commercially available are electrically erasable programmable random memories (EEPROMs) or indeed flash memories, and the invention can be used with any other programmable memory that may become available in the future.

Figure 2:
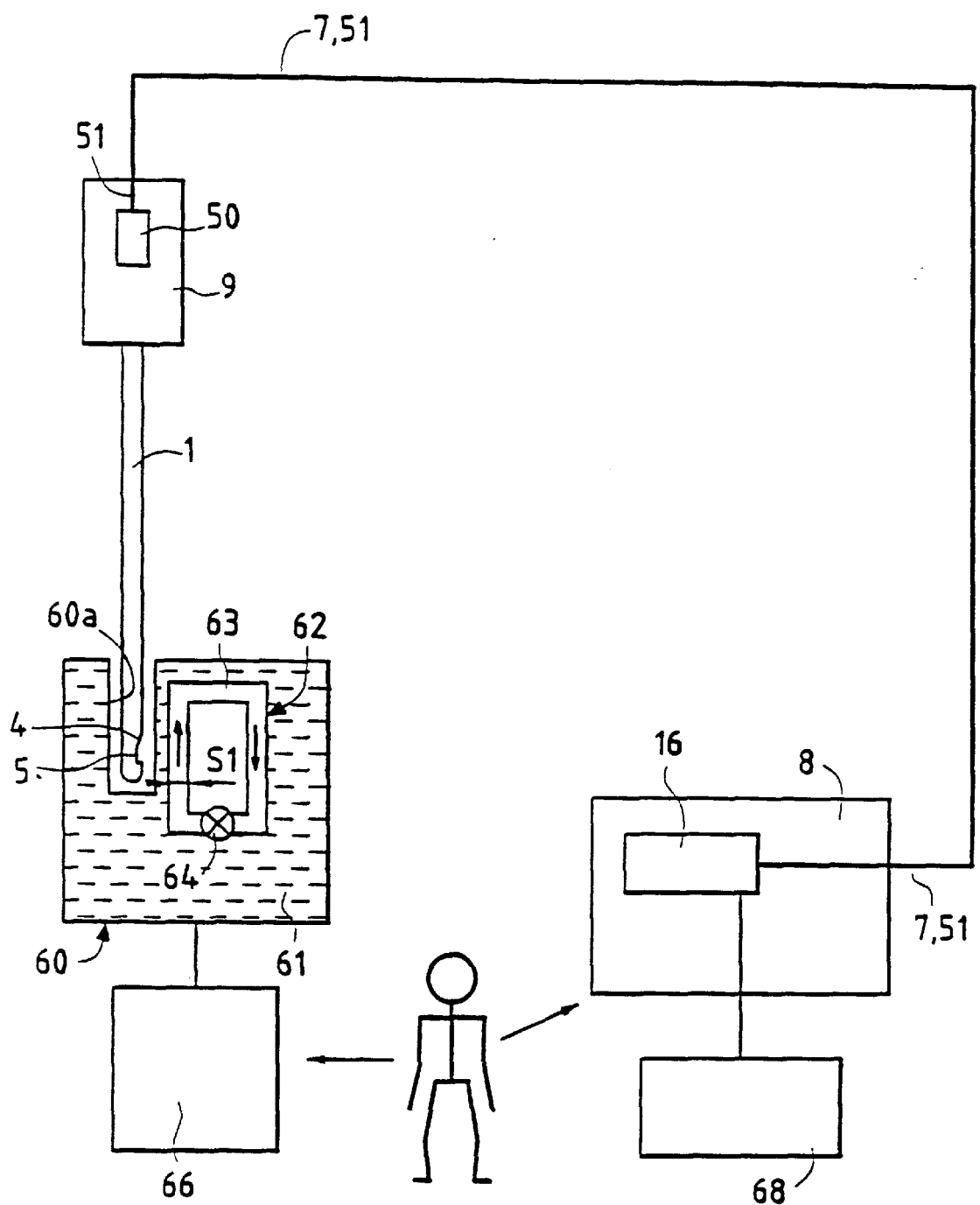
FIG. 2 is a diagram showing the operation of calibrating the FIG. 1 probe including the programmable memory in accordance with the invention so as to determine the characteristic of the Doppler transducer actually mounted on the probe.

With reference to FIG. 2, there is shown a diagram representing the operation of calibrating the FIG. 1 probe incorporating the programmable memory of the invention for the purpose of determining the characteristics of the Doppler transducer actually mounted in the probe, which characteristics are subsequently used for correcting the measured flow speed of the fluid F circulating in the duct 10. For this purpose, a tank 60 is provided that is filled with a liquid, such as water, and that has a well 60a which is filled with water and in which the active end of the probe 1 having the said transducers 4 and 5 is inserted. The well 60a thus symbolizes the esophagus 13 of a human body. The tank 60 has immersed therein a closed circuit 62 for circulating a fluid 63, such as water containing starch, so that the closed circuit 62 symbolizes the aorta 10 in which blood is flowing, and the flow section S1 of the closed circuit 61 is calibrated, e.g. to a value $S_1$ that is close to the flow section S of the blood vessel, so as to enable tests to be performed under conditions that are close to the genuine working conditions of the probe 1 when in the human body. The speed at which the liquid 63 flows round the closed circuit 62 is determined by acting on a pump or any other similar device for adjusting the flow speed of the liquid 63 in the closed circuit 62. The flow speed of said fluid is read by any appropriate flow measuring apparatus represented by 66. During these tests at its manufacturing site, the probe is connected to the control unit 8 which contains in particular the computation means 16 such as a computer or a microcomputer. A screen 68 is generally also provided on which various parameters are displayed together with the results obtained.

The tests performed comprise fixing the flow speed of the liquid 63 round the closed circuit 62 at various different values by means of the flow meter or spinner 64, thus making it possible to plot a calibration curve for the Doppler transducer 4.

Figure 3:
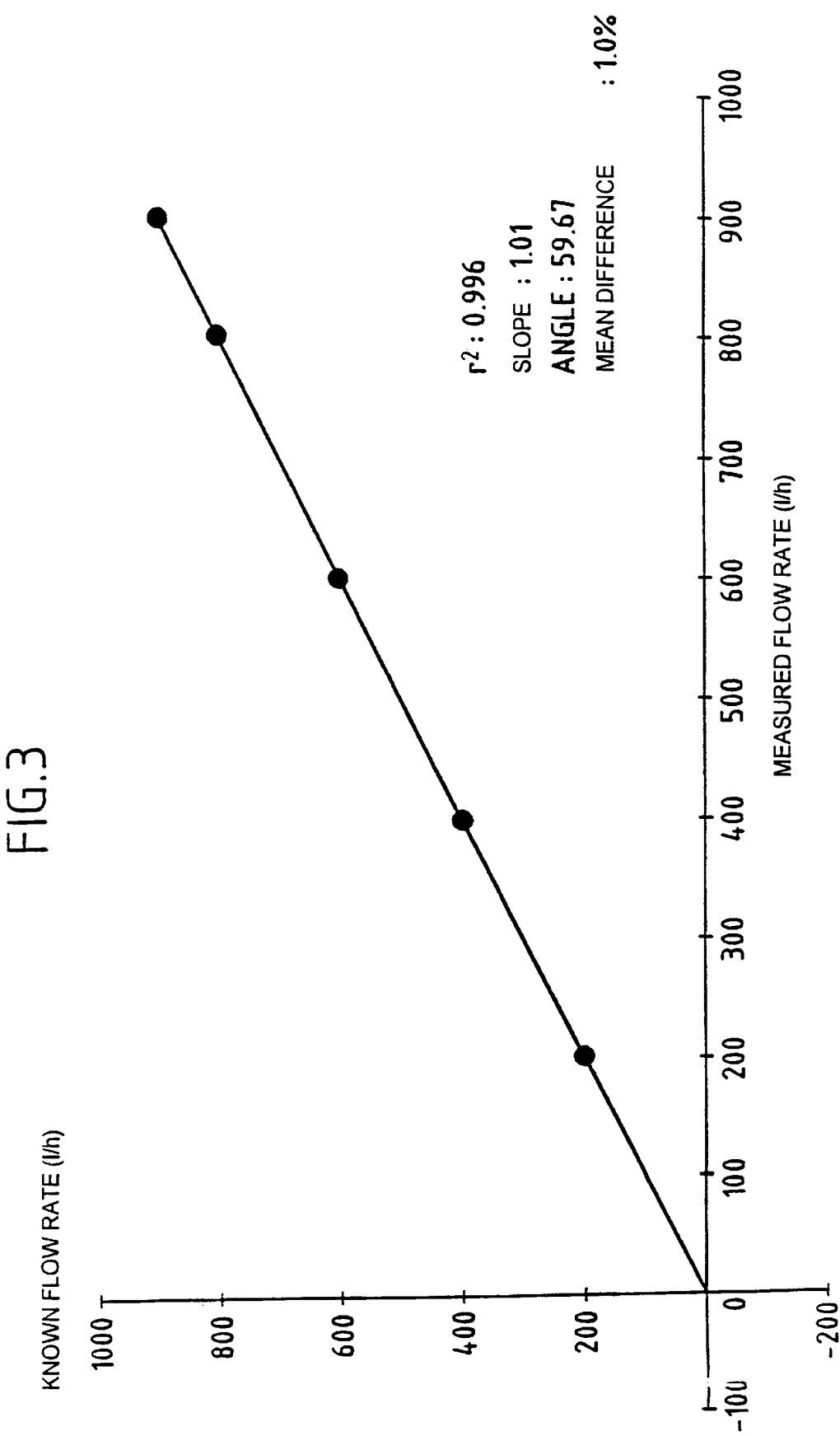
FIG. 3 is a calibration curve obtained during tests performed at the manufacturing site to calibrate the Doppler transducer 4 using the equipment of FIG. 2.

An example of such a calibration curve is given in FIG. 3.

In FIG. 3:
the ordinate (reference flow rate) corresponds to reference measurements as provided by the flow rate measuring apparatus 66 (FIG. 2); and
the abscissa (measured flow rate) corresponds to the measurements performed by means of the probe, assuming that the ultrasound beam is inclined at an angle θ of 60° ($\theta_{ideal}$=60°) and using the computation means 16 (FIG. 2) of the probe control and computer unit 8 (FIG. 2).

The curve and the estimated angle and linear regression correlation relating to the ultrasound beam are displayed on the screen 68 (FIG. 2).

The control unit 8 (FIG. 2) automatically saves the estimated angle (59.67° in this example) for the ultrasound beam in the memory of the probe 50 (FIG. 2).

From the equation mentioned above:

$$V \approx \frac{\Delta F}{F_{emit}} \times \frac{C}{2 \cdot \cos(\theta)}$$

it can be shown that:

$$\theta_{est.} = \text{ArcCos}\left(\frac{\text{reference flow rate}}{\text{measured flow rate}} \times \cos(\theta_{ideal})\right)$$

The ratio $$\frac{\text{reference flow rate}}{\text{measured flow rate}}$$

is obtained directly by the slope of the regression line through the points in FIG. 3.

What is claimed is:

1. A method for improving the accuracy with which the speed of a fluid, such as a liquid, in particular blood flowing in a duct, such as a blood vessel, in particular the aorta, is measured by means of a signal emitted by a Doppler transducer, wherein:

(a) the Doppler transducer is associated with a programmable memory containing at least one signal correction data item for correcting the Doppler signal transmitted by the transducer to a transducer control and computer unit;

(b) the computer unit incorporates the signal correction data item in computing each speed measurement on the basis of each signal emitted by the Doppler transducer, and computes the speed value taking account of the signal correction data item so as to provide a corrected measurement of the speed of the fluid, thereby improving the accuracy of the measurement;

(c) the signal correction data item is obtained from tests preferably performed at the manufacturing site while performing preliminary use tests on the Doppler transducer in order to verify the reliability of its signal; and (d) the signal correction data item comprises at least the angle at which the Doppler beam is emitted by the Doppler transducer relative to the axis of the probe, so that the speed value takes account of the real working angle of the beam from the Doppler transducer.

2. The method of claim 1, wherein the Doppler transducer is incorporated or integrated in a probe, in particular a Doppler effect intracorporeal probe, and the Doppler transducer is mounted on the probe to emit an ultrasound beam at an angle relative to the longitudinal axis of the probe, and wherein the probe also comprises the programmable memory.

3. The method of claim 1, wherein:

(a) the programmable memory also contains at least one sensitivity data item for informing the user of a loss of sensitivity to the Doppler signal;

(b) the transducer control and computer unit verifies the sensitivity data item present in the programmable memory on each measurement of the signal transmitted by the transducer in order to verify that the sensitivity actually obtained on the signal transmitted by the transducer is not too far removed from the sensitivity value present in the programmable memory; and (c) in the event of sensitivity going beyond a specified limit value, the transducer control and computer unit issues to the user a signal indicative of a loss of sensitivity.

4. The method of claim 3, wherein the sensitivity data item is obtained during tests that are preferably performed at the manufacturing site while measuring the flow speed of a fluid that is flowing at a known speed.

5. The method of claim 3, wherein the sensitivity data item comprises at least one average of a plurality of sensitivity measurements obtained over a corresponding number of uses of the Doppler transducer, each sensitivity measurement resulting from the amplitude of the signal received from the transducer.

6. The method of claim 3, wherein the transducer control and computer unit continuously computes the mean of a plurality of recently calculated sensitivity measurements and compares it with the sensitivity mean initially entered as sensitivity data into the programmable memory, and, beyond a certain difference relative to the initially programmed sensitivity measurement, issues a signal to the user indicative of a loss of sensitivity.

7. The method of claim 1, wherein, when the Doppler transducer operates in combination with an additional transducer, e.g., for measuring the diameter of a duct in which the fluid flows, at least one sensitivity data item concerning the additional transducer is preferably also provided in the programmable memory, so as to verify its sensitivity over time, and likewise issue a signal to the user in the event of a loss of sensitivity.

8. An apparatus for improving the accuracy with which the speed of a fluid, such as a liquid, in particular blood flowing in a duct, such as a blood vessel, in particular the aorta, is measured by means of a signal emitted by a Doppler transducer, said apparatus comprising a programmable memory containing at least one signal correction data item for correcting the Doppler signal transmitted by the transducer to a transducer control and computer unit, wherein:

(a) means are provided to enable the computer unit to incorporate the signal correction data item in computing each speed measurement on the basis of each signal emitted by the Doppler transducer, and to compute the speed value taking account of the signal correction data item so as to provide a corrected measurement of the speed of the fluid, thereby improving its accuracy;

(b) the signal correction data item is obtained from tests preferably performed at the manufacturing site while performing preliminary use tests on the Doppler transducer in order to verify the reliability of its signal; and (c) the signal correction data item comprises at least the angle at which the Doppler beam is emitted by the Doppler transducer relative to the axis of the probe, so that the speed value takes account of the real working angle of the beam from the Doppler transducer as actually created on the probe.

9. The apparatus of claim 8, wherein the Doppler transducer is incorporated or integrated in a probe, in particular a Doppler effect intracorporeal probe, and the Doppler transducer is mounted on the probe to emit an ultrasound beam at an angle relative to the longitudinal axis of the probe, and wherein the probe also comprises the programmable memory connected to the transducer control and computer unit, which memory is thus secured to the probe and is dedicated thereto.

10. The apparatus of claim 8, wherein:

(a) the programmable memory also contains at least one sensitivity data item for informing the user of a loss of sensitivity to the Doppler signal;

(b) the transducer control and computer unit verifies the sensitivity data item present in the programmable memory on each measurement of the signal transmitted by the transducer in order to verify that the sensitivity actually obtained on the signal transmitted by the transducer is not too far removed from the sensitivity value present in the programmable memory;

(c) signal-issuing means are provided; and (d) in the event of sensitivity going beyond a specified limit value, the transducer control and computer unit issues a signal to the user, via the signal-issuing means, to inform the user of a loss of sensitivity.

11. The apparatus of claim 10, wherein the sensitivity data item is obtained during tests that are preferably performed at the manufacturing site while measuring the flow speed of a fluid that is flowing at a known speed.

12. The apparatus of claim 10, wherein the sensitivity data item comprises at least one average of a plurality of sensitivity measurements obtained over a corresponding number of uses of the Doppler transducer, each sensitivity measurement resulting from the amplitude of the signal received from the transducer.

13. The apparatus of claim 12, wherein the transducer control and computer unit continuously computes the mean of a plurality of recently calculated sensitivity measurements and compares it with the sensitivity mean initially entered as sensitivity data into the programmable memory, and, beyond a certain difference relative to the initially programmed sensitivity measurement, issues a signal to the user, via the signal-issuing means, to indicate a loss of sensitivity.

14. The apparatus of claim 8, further comprising an additional transducer operating in combination with the Doppler transducer, said additional transducer being intended, for example, to measure the diameter of a duct in which the fluid flows, and said programmable memory preferably further containing at least one sensitivity data item concerning the additional transducer, so as to verify its sensitivity over time, and likewise issue, via the signal-issuing means, a signal to the user in the event of a loss of sensitivity.

* * * * *